(12) United States Patent
Coe (10) Patent No.: US 11,166,811 B2
(45) Date of Patent: Nov. 9, 2021

(54) TRANSCATHETER VALVE (71) Applicant: James Yashu Coe, Edmonton (CA)

(72) Inventor: James Yashu Coe, Edmonton (CA)

( * ) Notice: Subject to any disclaimer, the term of this patent is extended or adjusted under 35 U.S.C. 154(b) by 0 days.

(21) Appl. No.: 16/288,797

(22) Filed: Feb. 28, 2019

(65) Prior Publication Data

US 2019/0269507 A1 Sep. 5, 2019

Related U.S. Application Data

(60) Provisional application No. 62/637,618, filed on Mar. 2, 2018.

(51) Int. Cl.
*A61F 2/24* (2006.01)
*A61L 27/18* (2006.01)
(Continued)

(52) U.S. Cl.
CPC .......... *A61F 2/2418* (2013.01); *A61F 2/2415* (2013.01); *A61F 2/2433* (2013.01); *A61F 2/92* (2013.01); *A61L 17/00* (2013.01); *A61L 27/16* (2013.01); *A61L 27/18* (2013.01); *A61L 27/507* (2013.01); *A61L 27/56* (2013.01); *A61L 31/022* (2013.01); *A61F 2/24* (2013.01); *A61F 2/2412* (2013.01); *A61F 2/9522* (2020.05);
(Continued)

(58) Field of Classification Search
CPC ........ A61F 2/24; A61F 2/2412; A61F 2/2418; A61F 2/2433; A61F 2/92; A61F 2/9522; A61F 2220/0075; A61F 2230/0069; A61F 2240/001; A61L 17/00; A61L 27/18; A61L 31/022
See application file for complete search history.

(56) References Cited

U.S. PATENT DOCUMENTS 5,860,966 A 1/1999 Tower
8,075,615 B2 12/2011 Eberhardt et al.
(Continued)

FOREIGN PATENT DOCUMENTS

WO WO 95/11720 5/1995
WO WO 98/14137 4/1998

OTHER PUBLICATIONS

An Efficient Way to Make a Trileaflet Conduit for Pulmonary Valve Replacement; Chang et al.; The Society of Thoracic Surgeons; Published by Elsevier Inc.; © 2013; 3 pages.

*Primary Examiner* — Dinah Baria
(74) *Attorney, Agent, or Firm* — Barclay Damon LLP (57) ABSTRACT

A synthetic heart valve is made from a valve graft of synthetic material and more particularly expanded polytetrafluoroethylene (ePTFE). The valve graft has an upper portion defined by a first thickness and a lower portion defined by a second thickness which is greater than the first thickness. The valve graft is formed into a cylindrical sleeve having a diameter and a folded region. A flexible stent overlays the cylindrical sleeve, wherein a series of leaflets are formed in the lower portion of the sleeve, the leaflets defining a semicircular perimeter. The leaflets are sutured to the cylindrical sleeve and the cylindrical sleeve is sutured to the flexible stent, the stent having a plurality of bent cylindrical wire segments that are welded together and in which the sleeve is sutured to the wire, including the welded areas of the stent. The formed valve can be implanted using a balloon catheter.

5 Claims, 9 Drawing Sheets

(51) Int. Cl.
*A61L 27/50* (2006.01)
*A61L 31/02* (2006.01)
*A61L 17/00* (2006.01)
*A61F 2/92* (2013.01)
*A61L 27/56* (2006.01)
*A61L 27/16* (2006.01)
*A61F 2/95* (2013.01)

(52) U.S. Cl.
CPC ............... *A61F 2220/0075* (2013.01); *A61F 2230/0069* (2013.01); *A61F 2240/001* (2013.01)

(56) References Cited

U.S. PATENT DOCUMENTS

| | | |
|---|---|---|
| 8,511,244 B2 | 8/2013 | Holecek et al. |
| 8,961,599 B2 | 2/2015 | Bruchman et al. |
| 2006/0020327 A1* | 1/2006 | Lashinski ............ A61F 2/2439 623/1.25 |
| 2008/0262593 A1* | 10/2008 | Ryan ..................... A61F 2/852 623/1.12 |
| 2014/0288594 A1* | 9/2014 | Shaefers ................ A61L 17/10 606/222 |

* cited by examiner

TRANSCATHETER VALVE

CROSS REFERENCE TO RELATED APPLICATIONS

This application claims priority to U.S. Patent Application Ser. No. 62/637,618, filed Mar. 2, 2018, under relevant portions of 35 U.S.C. § 111 and 37 CFR §§ 1.51 and 1.53. The entire contents of this noted document is incorporated by reference in its entirety.

TECHNICAL FIELD

This application is directed generally to the field of heart valves and more specifically to a heart valve fabricated from a synthetic material and sutured to a flexible stent, the heart valve being configured for implementation using a balloon catheter delivery system.

BACKGROUND

Currently, heart valves from the cadavers of humans, referred to commonly as "homograft valves" have been implanted in living human subjects for decades. A primary problem with homografts is that of limited availability. To alleviate this problem, heart valves from animals, referred to commonly as "xenograft valves", and more specifically those from pigs, cows and sheep, are far more abundant. For example, porcine (pig) xenograft heart valves have been implanted in humans to replace damage or defective human heart valves since the early 1970s, particularly aortic heart valves.

Though the bovine jugular vein valve is approved and established to replace the pulmonary valve in human subjects, the range of sizes of a human subject may exceed that of the xenograft pulmonary heart valve. For example, the average diameter of men is about 29 mm and the average diameter for women is about 27 mm. The maximal bovine jugular vein valve for pulmonary valve replacement is 22 mm diameter. While pulmonary valves larger than 22 mm can be replaced using the Edwards Lifesciences Sapien valve, these biological valves degenerate over time and at an accelerated rate, if infected. Transcatheter valves made from synthetic materials (ePTFE) do not degenerate over time, and do not disintegrate in the presence of blood infection. Furthermore, there is an unlimited supply of ePTFE in all range of sizes. Still further, ePTFE valves also eliminate the unfounded fear of Jakob-Kreutzfeld disease.

As a result, there is a general need in the field to provide a heart valve that enables greater versatility for human subjects that is at least equal in terms of function and product life as homograft or xenograft heart valves.

BRIEF DESCRIPTION

Therefore and according to one aspect, there is provided a synthetic heart valve comprising a sheet or a cylinder that is made from a synthetic material and more particularly expanded polytetrafluoroethylene (ePTFE), the sheet having an upper portion defined by a first thickness and a lower portion defined by a second thickness which is greater than the first thickness, the sheet or cylinder being formed into a cylindrical sleeve having a diameter. In the instance of a sheet, the sheet further includes a folded region. A flexible stent is placed in overlaying position onto the formed cylindrical sleeve, wherein a plurality of valve leaflets are formed in the lower portion of the cylindrical sleeve, the valve leaflets each defined by a semicircular perimeter.

According to a preferred version, three (3) leaflets are formed, each having the semicircular perimeter that is sutured to the cylindrical sleeve. The cylindrical sleeve is sutured to the flexible stent, the stent comprising a plurality of wire segments formed into a cylindrical body, the wire segments being welded together at areas to define the cylindrical body, and in which the cylindrical sleeve is sutured to the wire segments of the stent, including the welded areas. According to at least one version, the wires of the flexible stent are made from a highly malleable material wherein the stent can be locally deformed. In one version, the stent is made from wire segments made from platinum and iridium. The sutures can also be made from ePTFE.

The herein described synthetic valve includes a plurality of valve leaflets that are configured to be movable between respective opened and closed positions. According to one version, the heart valve is defined by three (3) valve leaflets, forming a tricuspid valve that is manufactured by a single multi-layered sheet or a cylinder fabricated from ePTFE.

According to at least one version, the synthetic valve and flexible stent form an assembly that can be delivered for implantation by means of a balloon catheter.

According to another aspect, there is provided a method of manufacturing a synthetic heart valve, the method comprising the steps of providing a multilayered sheet made from a synthetic biocompatible material, cutting a plurality of valve leaflets from one layer of the sheet, rolling the sheet into a cylindrical sleeve, the rolled sheet having a folded area at connected ends thereof; suturing the valve leaflets to the formed cylindrical sleeve and suturing the cylindrical sleeve to a flexible stent. According to at least one embodiment and in lieu of a multilayered sheet, a cylinder made from the synthetic biocompatible material can be used as the valve graft. In the latter version, the folded area is eliminated.

An advantage realized by the herein described synthetic heart valve is that the valves can be manufactured over a greater range of valve diameters than xenograft heart valves presently available. The valves described herein do not deteriorate over time and also do not disintegrate in the presence of blood infection.

Another advantage is that the herein described heart valves can be manufactured by automation processes, making the overall assembly process less labor intensive.

These and other features and advantages will be readily apparent from the following Detailed Description, which should be read in conjunction with the accompanying drawings.

DETAILED DESCRIPTION

The following description relates to the manufacture of a heart valve (such as a pulmonary valve), fabricated from a graft formed from a specific synthetic biocompatible material, namely expanded polytetrafluoroethylene (ePTFE) in accordance with various embodiments. According to one embodiment, the graft is formed from a multi-layered sheet and according to another embodiment the graft is made from a cylinder made from the synthetic biocompatible material. As described herein, the heart valve is a tri-leaflet valve having a plurality (three) of semicircular leaflets, in which the formed graft or sleeve of the valve and the leaflets are sutured to a flexible stent for implementation to a patient site using a balloon catheter. It will be readily understood that there can be other variations and modifications of the herein described valve design herein intended to be within the ambits of the invention.

Figure 1A:
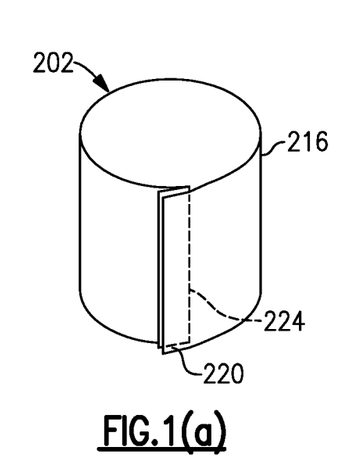
FIGS. 1(a)-1(b) represent sequential views of the manufacture of a synthetic valve in accordance with an embodiment.
Figure 1B:
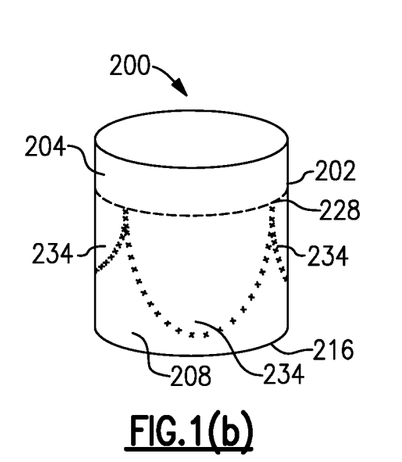

First, and with reference to FIGS. 1(a) and 1(b), the formation of a valve graft 200 in accordance with a first embodiment is herein described. The valve graft 200 is formed from a sheet 202 of expanded polytetrafluoroethylene (ePTFE), commonly referred to under the tradename of Gore-Tex®. The sheet 202 is cut initially longitudinally and is defined by a pericardial membrane having a thickness, according to this embodiment of 0.1 mm. The sheet 200 of the ePTFE material is further formed into a cylindrical sleeve having an upper portion 204 that is defined by a wall comprising of two layers (and therefore a thickness of 0.2 mm) and a lower portion 208 having a wall comprising of three layers (and therefore a thickness of 0.3 mm). The sheet 200 is formed into the cylindrical sleeve 216, as shown in FIG. 1(a). A folded region 220 is created at the respective edges of the sheet 200 to create a periphery having an interior diameter. The folded region 220 according to this embodiment is created proximate the respective edges of the sheet as formed by a vertically disposed fold line 224 extending over the height of the formed sleeve 216. When created the folded region 220, as herein represented, has a thickness in the upper portion 204 of 0.6 mm and a thickness in the lower portion 208 of 0.9 mm based on the overlap of sheet material in the folded region 220. According to this version, the folded region 220 is maintained by a continuous suture extending along the length of the fold line 224.

Figure 1C:
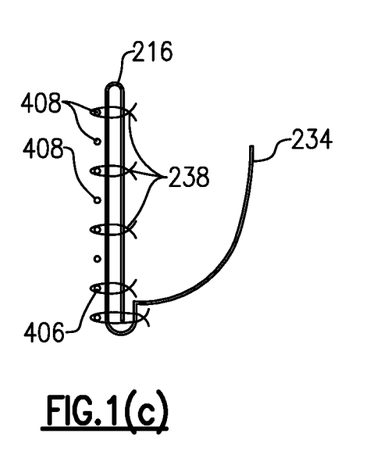
FIG. 1(c) depicts a partial assembly view taken in section depicting the securement of a valve leaflet by suturing to a flexible stent.

With reference to FIG. 1(b), the upper portion 204 and the lower portion 208 of the formed cylindrical sleeve 216 are divided (as shown by phantom line 228) and in which a series of connected leaflets 234 are formed in the lower (thickened) portion 208, as shown most closely in FIG. 1(b), indicating a total of three (3) identical valve leaflets 234. The leaflets 234 are each formed as semi-circular segments having a semi-circular perimeter that is sutured to the sleeve 216. The cylindrical sleeve 216 is secured by sutures 238 to the wire segments of a flexible stent 400, which is only partially shown in the vertical cross-sectioned view of FIG. 1(c). According to this embodiment, the sutures 238 which are also preferably made from ePTFE are CV-7 sutures having a diameter of 0.119 mm. Each formed valve leaflet 234 has a thickness of 0.1 mm and represents one layer of the formed graft 200.

Figure 2:
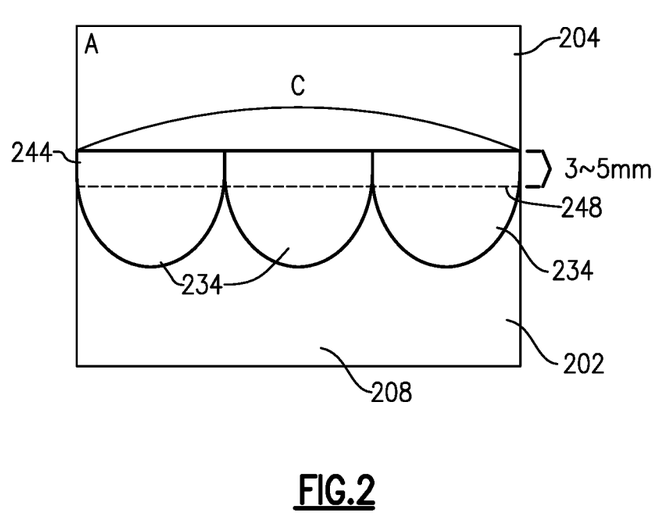
FIG. 2 is a longitudinal representation of the valve leaflets of a synthetic valve made in accordance with an embodiment.

FIG. 2 illustrates the three (3) leaflets 234 according to this tri-leaflet valve design, which includes the semicircular area of each leaflet 234 itself, the valve including a junction area or region 244 extending from the intersect point of adjacent leaflets and having a defined height dimension, shown by line 248, the junction region 244 extending along the entire circumference of the formed graft 200, which is shown in sheet form 202 in FIG. 2. In this example, the junction region above the dotted line is about 3-5 mm in height.

Figure 3:
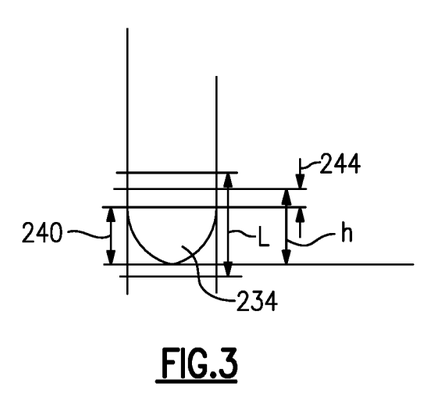
FIG. 3 is a detailed representation of a leaflet for a synthetic heart valve in accordance with an embodiment, the valve being made to an exemplary (specific) size.

With reference to FIGS. 2 and 3, the parameters of an exemplary synthetic valve leaflet and graft are herein described. More specifically, the herein described valve has a diameter (D) of 26 mm. The circumference of the valve is measured by a r (or 7C D). Therefore and according to this specific embodiment, the circumference c is equal to 81.68 mm. The width of each leaflet 234 of the valve is equal to one third the circumference c, since the valve is a tri-leaflet valve as shown in FIG. 2. Therefore, the width (W) of each valve leaflet 234 at the phantom line 248 defining the junction region 244 according to this embodiment is 27.23 mm. The height (h) of each valve leaflet 234 due to its semi-circular configuration is determined ($\sqrt{3}/2$)×the leaflet width (W). Therefore and for this specific valve, the height h is 23.58 mm, which includes the height of the junction region 244 as shown in FIG. 3. Based on the sample herein described, the valve leaflet radius (r) is determined by the height of the leaflet shown as 240×0.75. According to this embodiment, the value of r is equal to 17.68 mm. The height of the junction region 244 is defined as the leaflet height (h)−leaflet radius (r), which according to this embodiment is equal to 5.89 mm. Finally, the total length (L) of the valve according to this embodiment is determined by the height of the leaflets (h)+6 mm, the latter dimension being a margin of 3 mm added to the top and bottom of the valve graft 200. This latter dimension can be suitably varied. According to this specific version, the total length of the 26 mm diameter valve is 29.58 mm.

Alternatively and with reference to FIGS. 7A-7D, a valve graft in accordance with another embodiment can be made from a cylinder of ePTFE pericardial membrane having a wall thickness of 0.1 mm. The dimensions of the valve leaflets 334 are identical according to this version, with the exception of the elimination of the folded area previously required by the layered sheet, which therefore further eliminates 6 layers or 0.6 mm from the wall of the formed valve and accordingly reduces the profile of the valve. As discussed herein and when mounted on the balloon of a delivery catheter, the nominal wall thickness of the sheet made from ePTFE is 1.2 mm as compared to a reduced maximal wall thickness of 0.6 mm in the case of a sleeve formed from a cylinder of ePTFE creating a 50 percent reduction in overall material thickness.

The following table summarizes the above-described valve parameters for a range of diameters (D) made in accordance with this embodiment, the diameter range extending between 14 mm and 34 mm.

TABLE I

| π | Valve Diameter | Circumference | Width | Height | Leaflet radius | Junction | Total Length |
|---|---|---|---|---|---|---|---|
| 3.14 | 14.00 | 43.98 | 14.66 | 12.70 | 9.52 | 3.17 | 18.70 |
| 3.14 | 15.00 | 47.12 | 15.71 | 13.60 | 10.20 | 3.40 | 19.60 |
| 3.14 | 16.00 | 50.27 | 16.76 | 14.51 | 10.88 | 3.63 | 20.51 |
| 3.14 | 17.00 | 53.41 | 17.80 | 15.42 | 11.56 | 3.85 | 21.42 |
| 3.14 | 18.00 | 56.55 | 18.85 | 16.32 | 12.24 | 4.08 | 22.32 |
| 3.14 | 19.00 | 59.69 | 19.90 | 17.23 | 12.92 | 4.31 | 23.23 |
| 3.14 | 20.00 | 62.83 | 20.94 | 18.14 | 13.60 | 4.53 | 24.14 |
| 3.14 | 21.00 | 65.97 | 21.99 | 19.04 | 14.28 | 4.76 | 25.04 |
| 3.14 | 22.00 | 69.11 | 23.04 | 19.95 | 14.96 | 4.99 | 25.95 |
| 3.14 | 23.00 | 72.26 | 24.09 | 20.86 | 15.64 | 5.21 | 26.86 |
| 3.14 | 24.00 | 75.40 | 25.13 | 21.77 | 16.32 | 5.44 | 27.77 |
| 3.14 | 25.00 | 78.54 | 26.18 | 22.67 | 17.00 | 5.67 | 28.67 |
| 3.14 | 26.00 | 81.68 | 27.23 | 23.58 | 17.68 | 5.89 | 29.58 |
| 3.14 | 27.00 | 84.82 | 28.27 | 24.49 | 18.36 | 6.12 | 30.49 |
| 3.14 | 28.00 | 87.96 | 29.32 | 25.39 | 19.04 | 6.35 | 31.39 |
| 3.14 | 29.00 | 91.11 | 30.37 | 26.30 | 19.73 | 6.58 | 32.30 |
| 3.14 | 30.00 | 94.25 | 31.42 | 27.21 | 20.41 | 6.80 | 33.21 |
| 3.14 | 31.00 | 97.39 | 32.46 | 28.11 | 21.09 | 7.03 | 34.11 |
| 3.14 | 32.00 | 100.53 | 33.51 | 29.02 | 21.77 | 7.26 | 35.02 |
| 3.14 | 33.00 | 103.67 | 34.56 | 29.93 | 22.45 | 7.48 | 35.93 |
| 3.14 | 34.00 | 106.81 | 35.60 | 30.83 | 23.13 | 7.71 | 36.83 |

Figure 4:
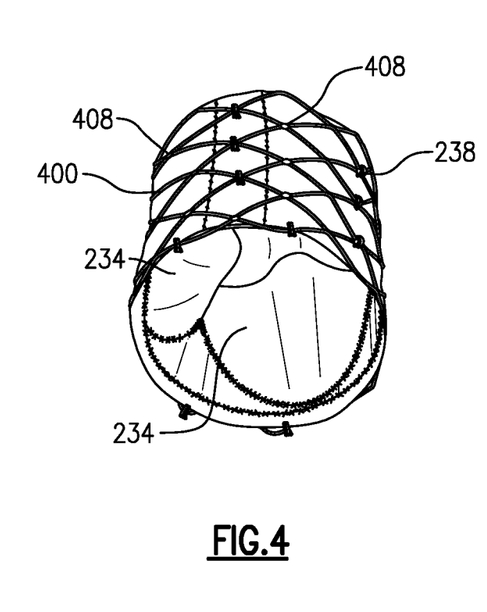
FIG. 4 is a bottom perspective view of an assembled synthetic valve in accordance with an embodiment.
Figure 5:
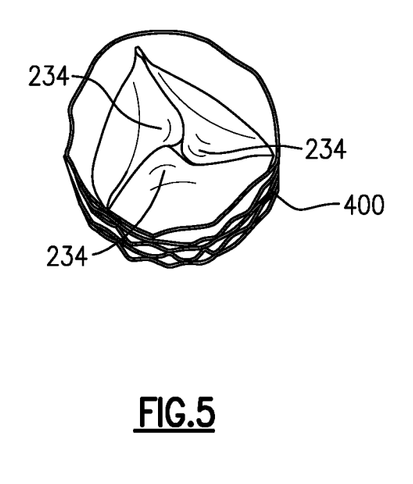
FIG. 5 is a top view of the assembled synthetic valve of FIG. 4.

With reference to FIGS. 4 and 5, a flexible stent 400 is placed in overlaying relation onto the formed ePTFE sleeve. For purposes of this discussion, the valve graft 200 is shown, although the cylindrical graft 300 would be similarly attached. The flexible stent 400 utilized according to this embodiment is defined by a cylindrical body that is made from a plurality of fine wire segments 406. The fine wire segments 406 are joined together to form a tubular or cylindrical member. Each wire segment 406 is fabricated from a soft, highly malleable metal alloy that has been fully annealed in order to remove as much spring memory as possible. Preferably and for purposes of this embodiment, the wire material is fabricated from an alloy consisting of about 90 percent platinum and 10 percent iridium and having a tensile strength of between about 150,000 psi and 175,000 psi. Although a platinum-iridium wire is preferred, other alloys having similar properties, such as, for example, a gold nickel alloy may also be employed. More specifically, each of the wire segments 406 have a diameter of 0.33 mm according to this exemplary embodiment. Prior to winding the wire segments 406 into a cylindrical shape, each section is formed so that it contains a series of alternating sinusoidal bends. The bends can be formed, according to one version, by winding each strand of wire between rows of vertical pins projecting from the surface of a flat planar substrate (not shown) as described in WO 95/11720 and WO 98/14137, the entire contents of each document being incorporated herein by reference. The strand can be wound about the pins to create a desired sinusoidal shape with the appropriate number of bends with a free length of wire at each end of the formed segment forming a serpentine pattern.

Each wire segment 406 is wound into a cylinder and the cylinders are placed in axial alignment so that the apex of each bend section is located in close proximity with the apex of a bend section of an adjacent wound segment. The adjacent bend sections are then welded together at weld joints 408 in order to cojoin the segments and form the cylindrical body. The fee ends of the adjacent cylindrical wire segments 406 are bent into parallel overlapping alignment and are also conjoined using similar welds.

Each weld joint 408 is formed, preferably, so that the weld joint 408 lies inside the boundaries of the cylindrical stent 400 as described by the inside diameter and the outside diameter of the formed cylinder. Accordingly, the weld joint 408 does not protrude beyond the boundaries of the wire cylinder into regions where rough edges of the welds 408 might come into contact with tissue. The platinum-iridium wires of the stent 400 are laser welded at each weld joint and brazed with 24 carat gold.

As noted, the flexible stent 400 is disposed in overlaying fashion onto the formed valve graft 200, which includes the valve leaflets 234 that are already sutured to the sleeve 216 using CV-7 Gore-Tex sutures having a diameter of 0.05 mm. The cylindrical sleeve 216 is sutured to the stent 400, which may include the weld joints 408, as shown pictorially in FIGS. 1(c), 4 and 5.

Figure 6:
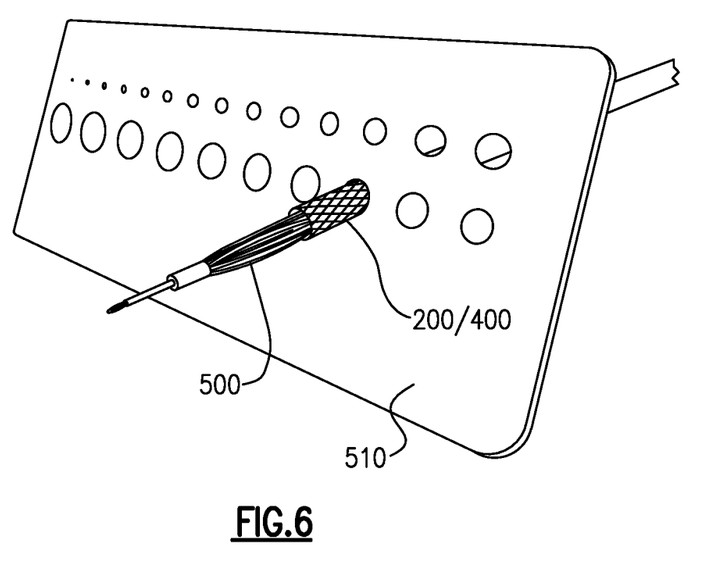
FIG. 6 illustrates an assembled synthetic valve as further assembled to a balloon catheter for purposes of implantation.
Figure 7A:
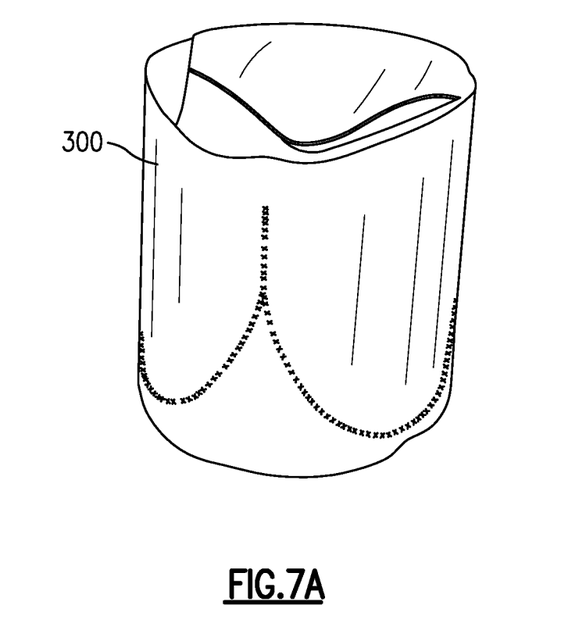
FIGS. 7A and 7B are representative views of a synthetic valve that is made in accordance with another embodiment.
Figure 7B:
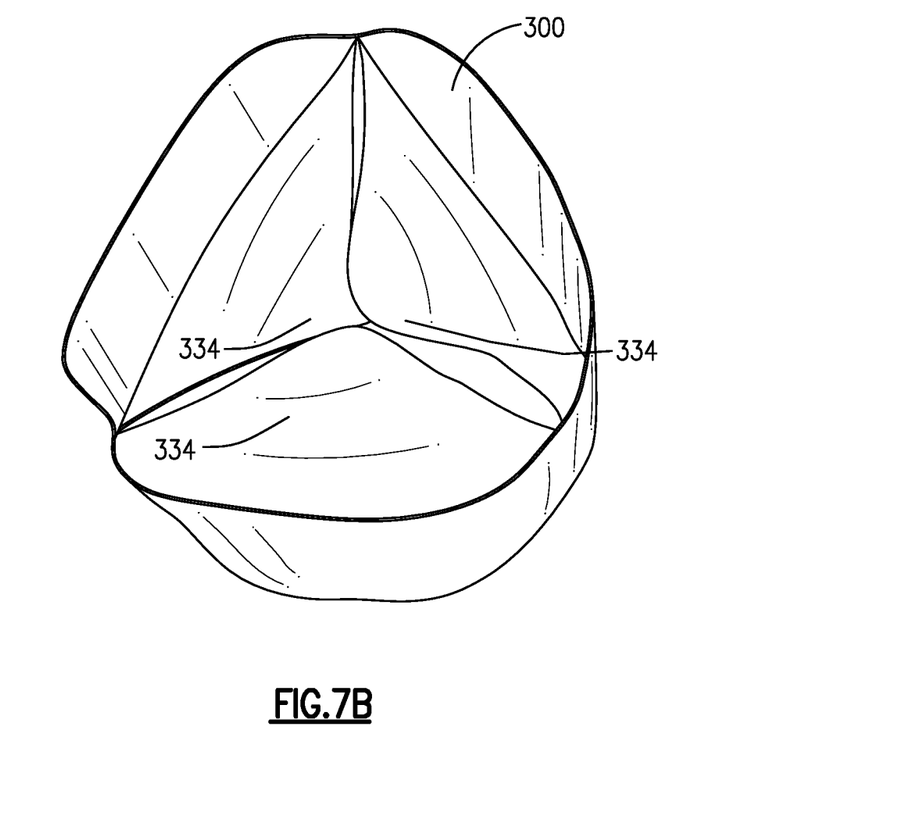
Figure 7C:
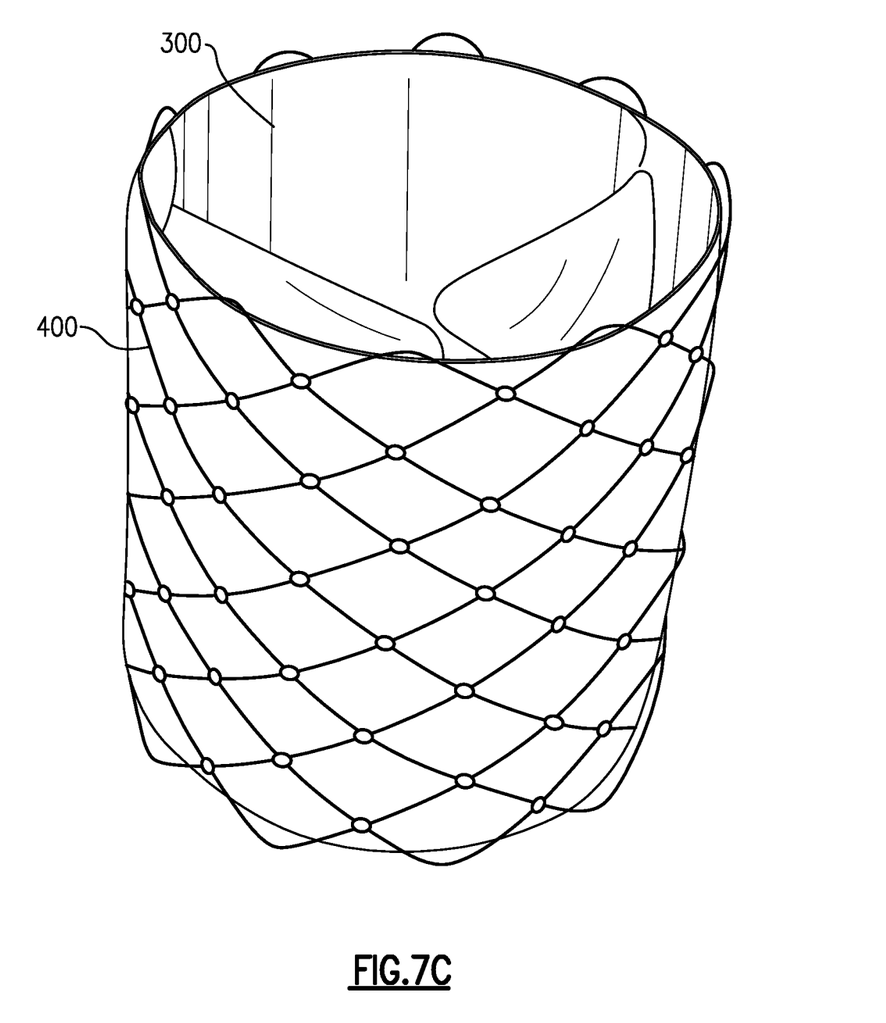
FIGS. 7C and 7D are representative view of the synthetic valve of FIGS. 7A and 7B as sutured to a flexible stent.
Figure 7D:
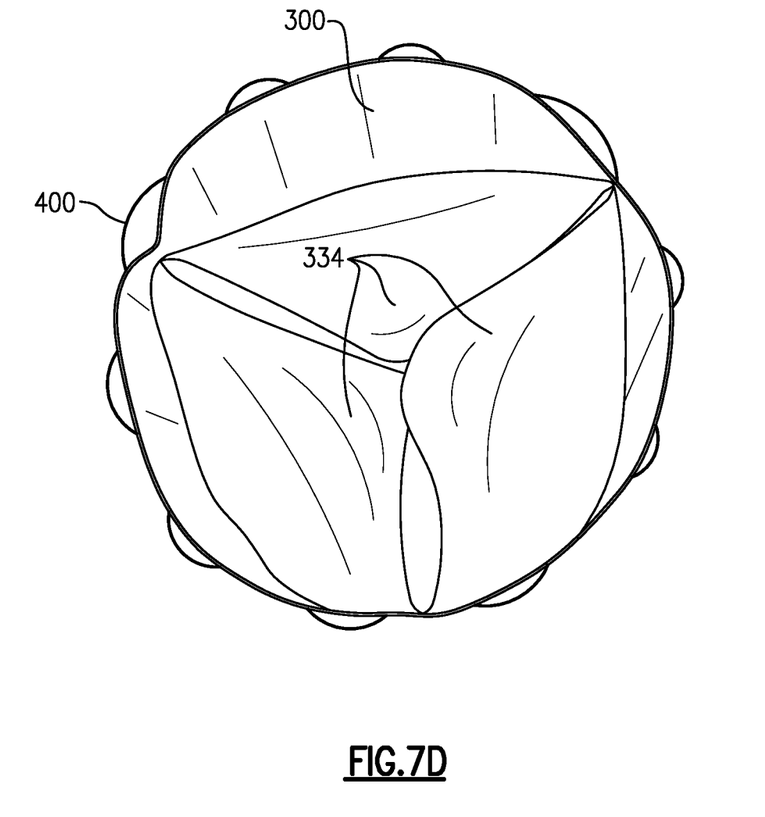

As shown in FIG. 6, a valve made in accordance with the present invention can be attached onto a balloon catheter 500, which is part of an implantation delivery system. An exemplary catheter is described in greater detail in U.S. Pat. No. 5,860,966, which is incorporated herein by reference in its entirety and a catheter such as the Balloon-in-Balloon (BIB) catheter commercially manufactured and sold by NuMed, Inc. of Hopkinton, N.Y. The annealed nature of the wire material of the formed flexible stent 400 permits the sutured valve graft to be radially expanded by the balloon in which the stent 400 is configured to maintain the expanded configuration after expansion and removal of the catheter to complete implantation at the patient site.

As shown in FIG. 6 and by way of specific example, a 20 mm valve is mounted to a 20 mm BIB balloon, fitting a FR 20 opening in a catheter scale 510.

PARTS LIST FOR FIGS. 1-7D 200 valve graft
202 sheet, synthetic material
204 upper portion
206 lower portion
216 cylindrical sleeve
220 folded region
224 fold line
228 phantom line
234 valve leaflets
238 sutures
240 height, leaflet
244 junction region or zone
248 line 300 valve graft
302 cylinder
334 valve leaflets
400 flexible stent
406 wire segments
408 welds or weld joints
500 balloon catheter
510 catheter scale It will be readily apparent that other variations and modifications are possible within the inventive ambits described herein and in accordance with the following claims. For example, other flexible intraluminar stents can be used in conjunction with the valve graft tube or cylinder or other suitable stent delivery systems.

The invention claimed is:

1. A synthetic heart valve comprising made up of:
a valve graft made from expanded polytetrafluoroethylene (ePTFE), the valve graft consisting of a series of layers and having an upper portion having a first thickness made up of two layers and a lower portion having a second thickness made up of three layers, the valve graft having a cylindrical configuration with a diameter; and
a flexible stent overlaying the valve graft, wherein a plurality of leaflets are formed in the lower portion in at least one of the layers of the valve graft, each of the leaflets having an arcuate portion defining a semicircular perimeter, each leaflet having a radius in which each leaflet is further defined by a height and a width including a junction region along a portion of the height of the leaflet in which the height of the junction region is defined by the height of the leaflet minus the radius of the leaflet, wherein a portion of each leaflet is sutured to the valve graft, the flexible stent comprising a plurality of wire segments that are welded together to form a cylindrical structure including a plurality of weld areas between adjacent wire segments, and the valve graft being sutured to the stent wherein the synthetic heart valve is a tricuspid valve having three leaflets in which the height of each leaflet is $\sqrt{3}/2$ times the width of the leaflet, the radius of each leaflet is equal to the height of the leaflet×0.75, and a total length of the valve is equal to the height of the leaflets+6 mm.

2. The valve according to claim 1, in which each of the plurality of wire segments of the stent are made from an alloy comprising platinum and iridium.

3. The valve according to claim 1, wherein sutures used to suture the valve graft to the stent are made from expanded polytetrafluoroethylene.

4. The valve according to claim 1, in which the wire segments of the flexible stent are formed in a pattern.

5. The valve according to claim 4, in which the synthetic heart valve is attachable to an inflatable balloon catheter used to implant the synthetic heart valve relative to a patient.

* * * * *